United States Patent
Hancock et al.

(10) Patent No.: US 11,246,657 B2
(45) Date of Patent: Feb. 15, 2022

(54) ELECTROSURGICAL RESECTION INSTRUMENT

(71) Applicant: CREO MEDICAL LIMITED, Chepstow (GB)

(72) Inventors: Christopher Paul Hancock, Bath (GB); Steven Morris, Bath (GB); Duncan Fitzsimmons, Greater London (GB); Brian Saunders, Hertfordshire (GB); Andrew Pacey, Stevenage (GB); Malcolm White, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 319 days.

(21) Appl. No.: 16/284,947

(22) Filed: Feb. 25, 2019

(65) Prior Publication Data
US 2019/0209237 A1    Jul. 11, 2019

Related U.S. Application Data

(63) Continuation of application No. 14/411,327, filed as application No. PCT/GB2013/051672 on Jun. 25, 2013, now Pat. No. 10,251,697.

(30) Foreign Application Priority Data

Jul. 3, 2012 (GB) .................................... 1211776

(51) Int. Cl.
*A61B 18/14* (2006.01)
*A61B 18/18* (2006.01)
(Continued)

(52) U.S. Cl.
CPC ........ *A61B 18/1492* (2013.01); *A61B 18/042* (2013.01); *A61B 18/1815* (2013.01);
(Continued)

(58) Field of Classification Search
CPC ............. A61B 18/042; A61B 18/1492; A61B 18/1815; A61B 2018/00107;
(Continued)

(56) References Cited

U.S. PATENT DOCUMENTS 5,246,440 A * 9/1993 Van Noord ........ A61B 18/1402
606/39
6,383,182 B1   5/2002 Berube et al.
(Continued)

FOREIGN PATENT DOCUMENTS

CN    1610526 A      4/2005
GB    2472972 A  *   3/2011  ............. A61B 18/18
(Continued)

OTHER PUBLICATIONS

International Search Report, International Application No. PCT/GB2013/051672, dated Sep. 26, 2013.
(Continued)

*Primary Examiner* — Tigist S Demie
(74) *Attorney, Agent, or Firm* — Arent Fox LLP

(57) ABSTRACT

An electrosurgical resection instrument for applying to biological tissue radiofrequency electromagnetic energy has a protective hull comprising a shaped piece of dielectric material mounted to cover an underside of an instrument tip of the instrument. The protective hull acts as a shield to protect tissue that may lie under the instrument tip from damage during treatment. The instrument may be particularly useful in procedures performed in a gastrointestinal tract, where bowel perforation is a concern, or in the pancreas, where damage to the portal vein or the pancreatic duct may occur when a tumor or other abnormality is being resected, dissected or removed.

24 Claims, 9 Drawing Sheets

(51) Int. Cl.
*A61B 18/04* (2006.01)
*A61B 18/00* (2006.01)
*A61B 90/00* (2016.01)
*A61B 18/12* (2006.01)

(52) U.S. Cl.
CPC ............... *A61B 2018/00107* (2013.01); *A61B 2018/00494* (2013.01); *A61B 2018/00994* (2013.01); *A61B 2018/128* (2013.01); *A61B 2018/1213* (2013.01); *A61B 2018/1405* (2013.01); *A61B 2018/1876* (2013.01); *A61B 2018/1892* (2013.01); *A61B 2090/0801* (2016.02); *A61B 2218/002* (2013.01)

(58) Field of Classification Search
CPC ........... A61B 2018/00494; A61B 2018/00994; A61B 2018/1213; A61B 2018/128; A61B 2018/1405; A61B 2018/1876; A61B 2018/1892; A61B 2090/0801; A61B 2218/002
See application file for complete search history.

(56) References Cited

U.S. PATENT DOCUMENTS

| | | |
|---|---|---|
| 6,606,515 B1 | 8/2003 | Windheuser et al. |
| 2003/0088242 A1* | 5/2003 | Prakash ............. A61B 18/1815 606/33 |
| 2003/0130658 A1 | 7/2003 | Goble et al. |
| 2005/0240151 A1 | 10/2005 | Hansmann et al. |
| 2006/0264929 A1 | 11/2006 | Goble et al. |
| 2007/0270757 A1 | 11/2007 | Willis et al. |
| 2010/0249769 A1 | 9/2010 | Nau, Jr. et al. |
| 2011/0196418 A1* | 8/2011 | Castro .................... A61B 17/29 606/205 |
| 2012/0283718 A1* | 11/2012 | Cosmescu .......... A61B 18/1402 606/33 |

FOREIGN PATENT DOCUMENTS

| | | |
|---|---|---|
| GB | 2487199 A | 7/2012 |
| JP | 2000-139942 A | 5/2000 |
| JP | 2005-512726 A | 5/2005 |
| WO | WO 2012/095653 A1 | 7/2012 |

OTHER PUBLICATIONS

Japanese Office Action of related Japanese Patent Application No. 2015-519332 dated May 23, 2017.

Communication from the State Intellectual Property Office of People's Republic of China in counterpart Application No. 201710874501.6, dated Aug. 1, 2019.

* cited by examiner

NEEDLE DEPLOYED

NEEDLE RETRACTED

ELECTROSURGICAL RESECTION INSTRUMENT

CROSS-REFERENCE TO RELATED APPLICATIONS

This application is a continuation of U.S. application Ser. No. 14/411,327, now Patent No. U.S. Pat. No. 10,251,697, filed Dec. 24, 2014, which is a National Stage entry of International Application No. PCT/GB2013/051672 filed Jun. 25, 2013, which claims the benefit of priority of United Kingdom Application No. 1211776.8 filed Jul. 3, 2012, the disclosure of these prior applications are hereby incorporated in their entirety by reference.

FIELD OF THE INVENTION

The invention relates to an electrosurgical device for delivering radiofrequency and/or microwave frequency energy into biological tissue. In particular, the invention relates to an electrosurgical instrument capable of delivering radiofrequency (RF) energy for cutting tissue and/or microwave frequency energy for haemostasis (i.e. sealing broken blood vessels by promoting blood coagulation). The invention may be particularly suitable in gastrointestinal (GI) procedures associated with the lower and upper GI tract, e.g. to remove polyps on the bowel, i.e. for endoscopic submucosal resection. The invention may also lend itself to precision endoscopic procedures, i.e. precision endoscopic resection, and may be used in ear, nose and throat procedures and liver resection. The device may also be used to address procedures associated with the pancreas, e.g. to resect or remove tumours or abnormalities in close proximity to the portal vein or the pancreatic duct.

BACKGROUND OF THE INVENTION

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, it is also undesirable for a bleed to occur and not to be dealt with as soon as quickly as possible, or in an expedient manner, since the blood flow may obscure the operator's vision, which may lead to the procedure needing to be terminated and another method used instead, e.g. open surgery.

Instead of a sharp blade, it is known to use radiofrequency (RF) energy to cut biological tissue. The method of cutting using RF energy operates using the principle that as an electric current passes through a tissue matrix (aided by the ionic contents of the cells), the impedance to the flow of electrons across the tissue generates heat. When a pure sine wave is applied to the tissue matrix, enough heat is generated within the cells to vaporise the water content of the tissue. There is thus a huge rise in the internal pressure of the cell, that cannot be controlled by the cell membrane, resulting in the cell rupturing. When this occurs over a wide area it can be seen that tissue has been transected.

Whilst the above principle works elegantly in lean tissue, it is less efficient in fatty tissue because there are fewer ionic constituents to aid the passage of electrons. This means that the energy required to vaporise the contents of the cells is much greater, as the latent heat of vaporisation of fat is much greater than that of water.

RF coagulation operates by applying a less efficient waveform to the tissue, whereby instead of being vaporised, the cell contents are heated to around 65° C. This dries out the tissue by desiccation and also denatures the proteins in the walls of vessels and the collagen that makes up the cell wall. Denaturing the proteins acts as a stimulus to the coagulation cascade, so clotting is enhanced. At the same time the collagen in the wall is denatured and changes from a rod like molecule to a coil, which causes the vessel to contract and reduce in size, giving the clot an anchor point, and a smaller area to plug.

However, RF coagulation is less efficient when fatty tissue is present because the electrical effect is diminished. It can thus be very difficult to seal fatty bleeders. Instead of having clean white margins, the tissue has a blackened, burned appearance.

In practice, a RF device may operate using a waveform with a medium crest factor that is midway between a cutting and coagulating output.

GB 2 472 972 describes an electrosurgical instrument in the form of a spatula comprising a planar transmission line formed from a sheet of a first dielectric material having first and second conductive layers on opposite surfaces thereof, the planar transmission line being connected to a coaxial cable that is arranged to deliver either microwave or RF energy to the planar transmission line, the coaxial cable comprising an inner conductor, an outer conductor coaxial with the inner conductor, and a second dielectric material separating the outer and inner conductors, the inner and outer conductors extending beyond the second dielectric at a connection interface to overlap opposite surfaces of the transmission line and electrically contact the first conductive layer and second conductive layer respectively. The first conductive layer is spaced from the end of the transmission line that abuts the coaxial cable to electrically isolate the outer conductor from the first conductive layer and also the distance of the gap is involved with matching the impedance of the energy delivered from the microwave source with the impedance of the biological tissue, and the width of the first and second conductive layers is also selected to help create an impedance match between the transmission line and the coaxial cable.

The spatula configuration set forth in GB 2 472 972 provides desirable insertion loss between the co-axial feed line and the end radiating section, whilst also providing desirable return loss properties for the edges of the spatula when in contact with air and biological tissue respectively. In more detail, the insertion loss along the structure may be less than 0.2 dB at the frequency of interest, and the return loss less than (more negative than) −1 dB, preferably less than −10 dB. These properties may also indicate a well matched junction between the coaxial cable and the transmission line spatula structure, whereby microwave power is launched efficiently into the spatula. Similarly, when the edges of the spatula are exposed to air or biological tissue that is not of interest, the return loss may be substantially zero (i.e. very little power radiated into free space or undesirable tissue), whereas when in contact with desirable biological tissue the return loss may be less than (more negative than) −3 dB, preferably less than −10 dB (i.e. the majority of power in the spatula is transferred to the tissue).

The instrument discussed in GB 2 472 972 is intended to radiate microwave energy from the edges of the planar transmission line to cause localised tissue ablation or coagulation.

GB 2 472 972 also discloses that the spatula discussed above may have an RF cutting portion integrated therewith. The RF cutting portion may be formed by using the first and second conductive layers mentioned above as active and return electrodes for RF energy. This arrangement may take advantage of the fact that the active and return electrodes are in close proximity to one another, thus setting up a preferential return path to enable local tissue cutting action to take place without the need for a remote return pad or a highly conductive liquid, i.e. saline, existing between the two electrodes.

In this example, the RF cutting portion may comprise a RF voltage source coupled to the planar transmission line, a frequency diplexer/duplexer unit (or signal adder) comprising a low pass filter to prevent the high frequency microwave energy from going back into the lower frequency RF energy source and a high pass filter to prevent the lower frequency RF energy from going back into the higher frequency microwave energy source. In one example, the frequency diplexer/duplexer may be used to enable the microwave and RF energy sources to be combined at the generator and delivered along a single channel, e.g. co-axial cable, waveguide assembly or twisted pair, to the spatula structure. The RF cutting energy may be delivered alone into the tissue or it may be mixed or added with the microwave energy and delivered simultaneously to set up a blended mode of operation.

SUMMARY OF THE INVENTION

At its most general, the present invention provides a development to the spatula concept discussed in GB 2 472 972 in which the underside of the spatula includes a protective hull comprising a shaped piece of dielectric material which overlies the lower conductive layer and acts as a shield to protect tissue that may lie under the spatula from damage during treatment. The protective hull may be particularly useful in procedures performed in the gastrointestinal tract, where bowel perforation is a concern, or in the pancreas, where damage to the portal vein or the pancreatic duct may occur when a tumour or other abnormality is being resected, dissected or removed.

The protective hull may be applied to spatulas adapted for different functions. For example, aspects of the invention contemplated herein include: a spatula adapted to deliver radiofrequency (RF) energy for cutting biological tissue; a spatula adapted to deliver both RF and microwave frequency energy separately or simultaneously; and a spatula adapted to deliver RF and/or microwave energy and having a retractable needle for delivering or removing fluid (liquid or gas) to or from the treatment site. For example, the needle may be used to introduce a gas, e.g. argon, to produce thermal or non-thermal plasma for surface coagulation (thermal) or sterilisation (non-thermal). The RF and/or microwave field may be used to strike and sustain or create this plasma. The protective hull may include a passageway, e.g. recessed channel, through which the retractable needle travels or through which fluid can be delivered without the use of a needle, e.g. for clinical or cleaning purposes.

According to the invention, there may be provided an electrosurgical resection instrument for applying to biological tissue radiofrequency (RF) electromagnetic (EM) energy, the instrument comprising: an instrument tip comprising a planar body made of a first dielectric material separating a first conductive element on a first surface thereof from a second conductive element on a second surface thereof, the second surface facing in the opposite direction to the first surface; a coaxial feed cable comprising an inner conductor, an outer conductor coaxial with the inner conductor and a second dielectric material separating the inner and outer conductors, the coaxial feed cable being for conveying an RF signal; and a protective hull comprising a third piece of dielectric material mounted to cover the underside of the instrument tip, wherein the inner conductor is electrically connected to the first conductive element and the outer conductor is electrically connected to the second cutting element to enable the instrument tip to receive the RF signal, wherein the first and second conductive elements are arranged to act as active and return electrodes to emit RF EM radiation corresponding to the RF signal from distal side portion of the planar body, and wherein the protective hull has a smoothly contoured convex undersurface facing away from the planar body.

The first and second conductive elements may be arranged to provide a local return path for RF energy, i.e. a low impedance route for RF energy to be transported between the first and second conductive elements. The first and second conductive elements may be layers of metallisation formed on opposite surfaces of the first dielectric material. The first and second conductive elements may be arranged to set up a local electric field at a contact region in which the instrument tip makes contact with the biological tissue. The local electric field can be extremely high, which may cause a microplasma (i.e. a hot thermal plasma) to be formed at the distal side portion of the planar body, e.g. where contact is made with the biological tissue. The microplasma may be desirable in terms of achieving efficient cutting. The first and second conductive elements may include portions, e.g. plated regions at and adjacent the distal side portion, made from conductive material having a high melting point, e.g. 1500° C. or more, such as titanium, tungsten or the like. Using such materials may prevent the high temperatures of the microplasma from eroding the first and second conductive elements. The first and second conductive elements may also include connecting portions made from conductive materials having lower melting points (e.g. silver, gold and the like) deposited or plated on the higher melting point conductors. The connecting portions may facilitate connection of the inner and outer conductors of the coaxial cable, e.g. by soldering or the like. In one embodiment, a titanium tungsten (TiW) seed layer may be used with a layer of silver (Ag) or gold (Au) deposited on the top. The lower melting point material may be deposited onto the higher melting point material only in the region where the coaxial cable inner and outer conductors are to be attached, i.e. at the proximal end of the instrument only, and not along the sides thereof, where the microplasma will be generated. This arrangement follows from the fact that the electric field at the point where the coaxial transmission line connects to the planar transmission line should be relatively low and so the temperature at this point should be much lower than the melting point of the lower melting point material.

The layers of metallisation may be formed from biocompatible materials, e.g. any of silver, titanium and gold. Table 1 below gives the melting and boiling points for materials considered for this device:

TABLE 1

Melting and Boiling Points for conductive materials
suitable for use on the instrument tip

| Material | Melting Point (° C.) | Boiling Point (° C.) |
|---|---|---|
| Tungsten (W) | 3422 | 5555 |
| Titanium (Ti) | 1668 | 3287 |
| Silver (Ag) | 961.78 | 2162 |
| Gold (Au) | 1064.18 | 2856 |

In one embodiment, the first dielectric material separating the conductive elements may provide the preferential return path between the inner conductor (active) and the outer conductor (return). RF tissue cutting may be produced at the distal side portion of the instrument tip if the first dielectric material has a high dielectric constant (e.g. greater than that of air) and the thickness of the first dielectric material at the distal side portion, i.e. the separation of the first and second conductive elements at the distal side portion edge, is small, i.e. less than 1 mm. This arrangement may provide the necessary preferential return path for the current to flow.

The undersurface of the protective hull may smoothly taper at its perimeter to meet the side of the planar body. The thickness of the protective hull may also decrease towards the distal end of the instrument tip. Thus, the outer portion of the protective hull may have a convex profile. The undersurface may have a longitudinally extending recessed channel formed therein. The tapering edge profile and recessed channel may cause the undersurface of the protective hull to comprise a pair of ridges. This shape may reduce the risk of the instrument digging into the bowel wall and causing a bowel perforation or may protect the portal vein or pancreatic duct from being damaged. The particular dimensions of the hull (e.g. length, width, thickness, etc.) may be adapted to suit the intended use and intended area of the body to be operated on.

The protective hull may be formed from a biocompatible non-conductive material, such as ceramic or biocompatible plastic that does not stick to the wall of the bowel (or other biological tissue) or the like. Alternatively, the hull may also be formed from a metallic material, e.g. titanium, steel, or may be a multi-layer structure. It may be attached (e.g. bonded) to whichever one of the first or second conductive elements is on the underside of the first dielectric material. However, in one embodiment, the protective hull may be formed of the same material as the first dielectric material. The protective hull and first dielectric material may be formed in one piece as a unitary body. In this arrangement one or more planar slots may be formed (e.g. cut) in the unitary body to allow a conductive material to be inserted to form the first and/or second conductive material.

The instrument tip may be curved at its distal end between the side edges of the planar body. The curve may describe a parabola in the plane of the planar body. The distal end of the protective hull may be curved in a similar manner. This shape prevents the instrument tip from presenting sharp corners to the biological tissue. This shape may also enable cutting to be performed in a direction diagonal to the long axis of the device, in addition to cutting in the same direction or in a direction perpendicular to the long axis.

The instrument may include a fluid feed conduit for delivering fluid (e.g. saline) to the instrument tip. The fluid feed conduit may comprise a passageway through the protective hull for delivering fluid to the treatment site. The passageway may include an outlet located in the recessed channel of the protective hull. The fluid (liquid or gas) may be conveyed to the instrument (protective hull) through a corresponding passageway formed within the coaxial feed cable. The fluid feed conduit may also be used to deliver other material to the treatment site, e.g. a gas or a solid (e.g. powder). In one embodiment, injection of fluid (saline or the like) is used to plump up the biological tissue at the treatment site. This may be particularly useful where the instrument is used to treat the wall of the bowel or the wall of the oesophagus or for protecting the portal vein or the pancreatic duct when a tumour or other abnormality located in close proximity, in order to protect these structures and create a cushion of fluid. Plumping up the tissue in this manner may help to reduce the risk of bowel perforation, damage to the wall of the oesophagus or leakage of from the pancreatic duct or damage to the portal vein, etc. This aspect of the invention may make it capable of treating other conditions where the abnormality (tumour, growth, lump, etc) is close to a sensitive biological structure.

It is advantageous to be able to use the same instrument to deliver fluid as delivers RF and/or microwave energy since deflation (e.g. due to fluid seepage) may occur if a separate instrument is introduced into the region or during treatment. The ability to introduce fluid using the same treatment structure enables the level to be topped up as soon as deflation occurs. Moreover, the use of a single instrument to perform desiccation or dissection as well as to introduce fluid also reduces the time taken to perform the overall polyp removal procedure, reduces the risk of causing harm to the patient and also reduces the risk of infection. More generally, injection of fluid may be used to flush the treatment region, e.g. to remove waste products or removed tissue to provide better visibility when treating. As mentioned above, this may be particularly useful in endoscopic procedures.

The fluid feed conduit may include a needle (e.g. hypodermic needle) mounted beneath the planar body in the recessed channel of the protective hull. The protective hull may include a guide passage for receiving the fluid feed conduit. The needle may have an outer diameter less than 0.6 mm, e.g. 0.4 mm. The needle may be movable in the longitudinal direction between a deployed position in which it protrudes beyond the distal end of the instrument tip and a retracted position in which it is set back from the distal edge of the instrument tip, e.g. below the planar body or locates proximal to the planar body. The needle may be open to fluid flow at the proximal end or side of the needle and may be moved using one or more control wires. For example, the proximal end of needle may be open to the passageway formed within the coaxial feed cable. The needle may be mounted in a through hole formed in the protective hull. The needle may be formed an slidable interference fit with the through hole, where it plugs the through hole to create a fluid path of least resistance through the needle when it is in the deployed position. This arrangement may prevent leaks from other parts of the instrument tip. The through hole may be formed by a tube or similar close-fit bearing surface mounted or formed at the underside of the protective hull, e.g. in the recessed channel.

The instrument may include a sleeve for conveying the coaxial cable, fluid feed conduit (if present) and control wire(s) (if present) to the instrument tip body. The instrument tip body and protective hull may be secured (e.g. bonded) into a distal end of the sleeve. The sleeve may include longitudinal braids to assist in the transfer of torque from its proximal end to the instrument tip. In one embodiment, the braided cable may be made from Pebax® material, and may comprise a plastic outer jacket with a metal braid attached at or to its inner wall. This type of sleeve may provide useful torque stability, whereby a twisting force applied to a handle attached to a proximal portion of the outer jacket of the sleeve is transformed accurately to a rotation motion of the instrument at the distal end of the sleeve. Preferably, the translation between the proximal end and the distal end is one to one (1:1), i.e. a twist of 20° at the proximal end should lead to a 20° rotation of the instrument tip.

The needle is slidably movable with respect to the protective hull through one or more control wires, which may be actuated via a suitable slide actuator at a proximal end of the instrument. Preferably, the needle is slidable back and forth with respect to a fluid supply passageway which conveys the fluid to the needle for delivery. The fluid supply passageway may be an integral part of the sleeve, or may be a tube statically mounted in the sleeve. The ability to move the needle back and forth while conveying fluid to the needle through a conduit which does not move relatively to the sleeve enables a retractable needle to be provided within a smaller diameter sleeve than a device in which a fluid delivery tube must slide along the length of the sleeve.

The sleeve may comprise a multi lumen tube. The lumens may be formed by inserting an extruded separator element inside a single lumen tube. The extruded separator element may include a U-shaped channel for guiding the coaxial cable and one or more through holes for carrying the fluid feed conduit and control wire(s).

The diameter of the sleeve is preferably less than 2.8 mm to enable it to fit down the instrument channel of an endoscope. The handle for applying torque to the sleeve may be located at the proximal end of the sleeve, near the endoscope controls.

The instrument may include a cap element at the distal end of the sleeve, the cap element covering the electrical joint between the coaxial cable and the first and second conductive elements. The cap element may be formed from a heat shrink material or from potting adhesive. Protecting the joint in this way may prevent arcing from occurring at the electrical joint during use. In particular, the cap element is arranged to seal the distal electrical connections from fluid at the instrument tip. Ingress of fluid to the junction where the co-axial cable is connected to the parallel plate planar transmission line is undesirable, as either the microwave energy may be absorbed, which will lead to heating and the energy not being delivered along the edge of the blade in an efficient manner, or the device will breakdown or flashover due to the lower breakdown voltage. The potting adhesive may comprises a combination of glues, e.g. low viscosity and high viscosity UV curing medically approved glues may be used such as Loctite® 4304 or Loctite® 4305, the low viscosity adhesive being useful for filling gaps, and the low viscosity being useful for wicking the adhesive into very fine potential fluid paths.

The instrument tip may also be arranged to receive microwave frequency energy. The coaxial cable may be arranged to convey a microwave signal separately from or simultaneously with the RF signal. The first and second conductive elements may be arranged on the first dielectric element to act as a near field antenna to radiate microwave EM radiation corresponding to the received microwave signal.

This embodiment may make use of the ability of the instrument to be "seen" differently by the RF signal and microwave signal. For the RF signal, the instrument tip may be modelled as a parallel plate capacitor. The electric field set up by the RF signal between the first and second conductive elements can be substantially contained with the planar body (first dielectric material) by setting the edges of the first and second conductive layers back from the side edges of the planar body. To perform RF cutting, it is desirable for the field to extend outside the planar body. In this invention it is possible to do this be extending the edges of the first and second conductive layers up to the side edge of the planar body in a region designated as an RF cutting portion. The RF field set-up between the two plates of the parallel plate capacitor (or planar transmission line) and coupled into the biological tissue, through making contact with one or more edges of the blade, may create a controlled microplasma and the microplasma may enable or enhance the tissue cutting process.

Meanwhile, for the microwave signal, the instrument tip may be modelled as a parallel plate transmission line with the planar body representing dielectric material separating two conductive plates. The radiation pattern of the microwave frequency EM energy in this case depends on the overall shape of the planar body and the microwave feed structure. In this particular instance, the gap at the proximal end between the co-axial feed line (centre conductor) and the upper conductive layer plays an important role in ensuring that the microwave energy from the source is matched in terms of impedance with the load impedance presented by the tissue. The overall length of the planar transmission line arrangement is also important in terms of matching the impedance (or the energy delivery) of (or from) the coaxial transmission line with (or into) the biological tissue, i.e. the structure may form a quarter wave impedance transformer or a half wavelength resonator. Using known simulation tools, this may be modelled to control from which edges the microwave frequency EM energy is radiated. For example, the instrument tip may be configured to inhibit radiation of the microwave EM radiation from a distal edge of the planar body.

Herein, radiofrequency (RF) may mean a stable fixed frequency in the range 10 kHz to 300 MHz and microwave frequency may mean a stable fixed frequency in the range 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz. Preferred spot frequencies for the microwave energy include 915 MHz, 2.45 GHz, 5.8 GHz, 14.5 GHz, 24 GHz.

BRIEF DESCRIPTION OF THE DRAWINGS

Embodiments of the invention are discussed in detail below with reference to the accompanying drawings, in which.

DETAILED DESCRIPTION; FURTHER OPTIONS AND PREFERENCES

Figure 1:
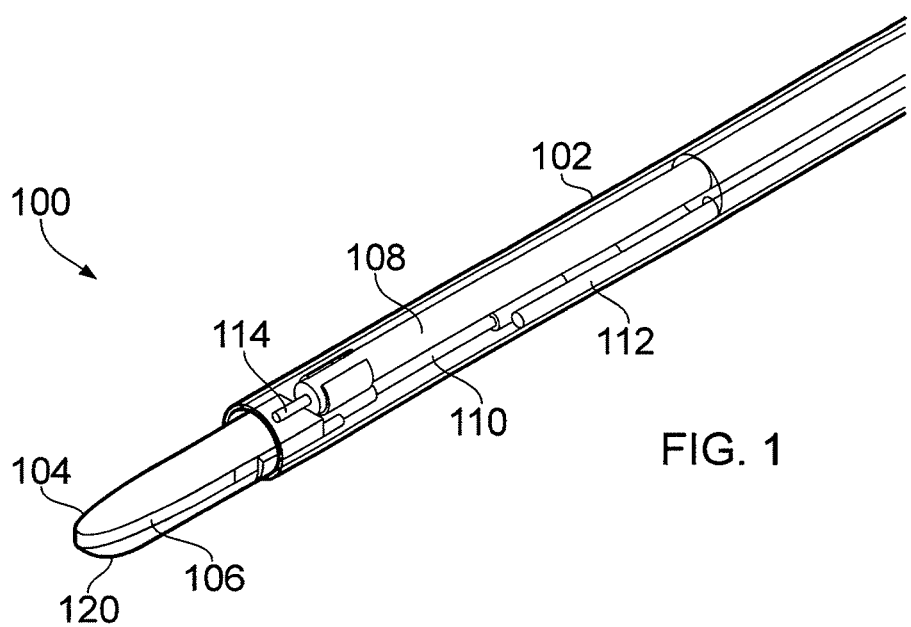
FIG. 1 is a partly transparent perspective view of an electrosurgical instrument that is an embodiment of the invention.

An electrosurgical instrument 100 that is an embodiment of the invention is now described with reference to FIGS. 1 to 9. The instrument comprises a sleeve 102 having an instrument tip 104 connected at its distal end. The sleeve 102 is made from a flexible polymer material (e.g. Pebax®) having axially-extending braids (e.g. of metal) encapsulating within it. This arrangement forms a torque stable system. The braids may not extend right up to the distal end of the sleeve, thus introducing a safe distance (e.g. of no less than 1 mm as measured along the longitudinal axis between the end of the braid and the proximal edge of the instrument tip in order to avoid any risk of heating of the braid as a result of capacitive conductance during use of microwave energy. A sleeve without braid may extend across this safe distance gap. This arrangement also prevents the two plates of the planar transmission line or the two conductors in the co-axial transmission line from becoming shorted or connected together. The braid structure enables torque applied to the proximal end of the sleeve to be accurately transformed into rotational movement of the instrument tip 104. For convenience, the sleeve 102 is shown as transparent in the drawings to permit illustration of its internal components. In practical embodiments, the sleeve may be opaque.

The instrument tip 104 comprises a dielectric block 106 that has layers of metallisation 105, 107 on its upper and lower surfaces. The layers of metallisation correspond to the first and second conductive elements of the invention. The layers of metallisation are separated by the thickness of the dielectric block 106 to form a bipolar radiating spatula structure, similar to that disclosed in GB 2 472 972.

The layers of metallisation may be formed from high melting point conductors, e.g. W or Ti. In such an arrangement, lower melting point conductors may be deposited around the regions where the coaxial cable connects to the parallel plate planar transmission line to facilitate soldering the coaxial arrangement to the planar transmission line. The lower melting point conductors may be silver (Ag) or gold (Au).

Figure 2:
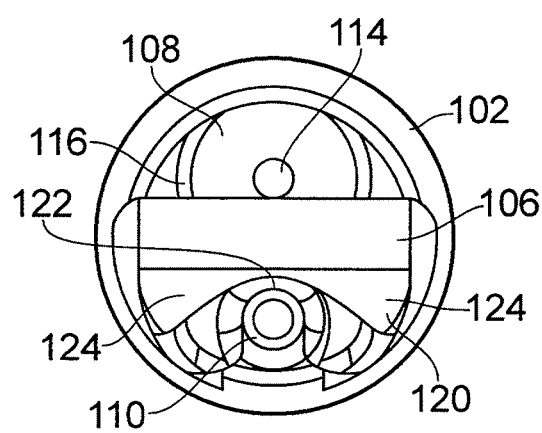
FIG. 2 is a front view of the instrument of FIG. 1.
Figure 3:
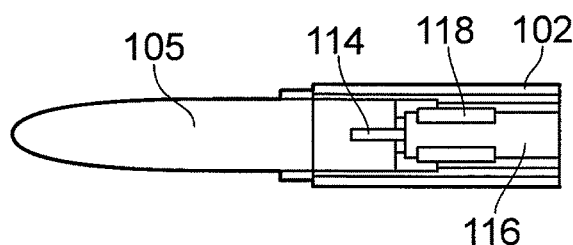
FIG. 3 is a top view of the instrument of FIG. 1.
Figure 4:
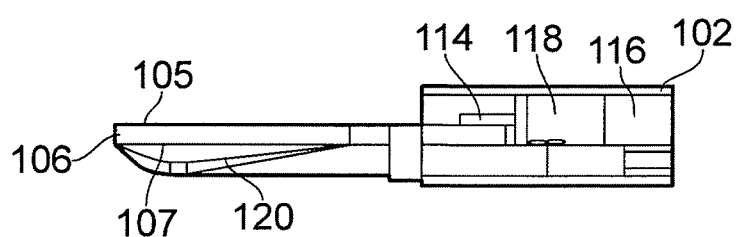
FIG. 4 is a side view of the instrument of FIG. 1.
Figure 5:
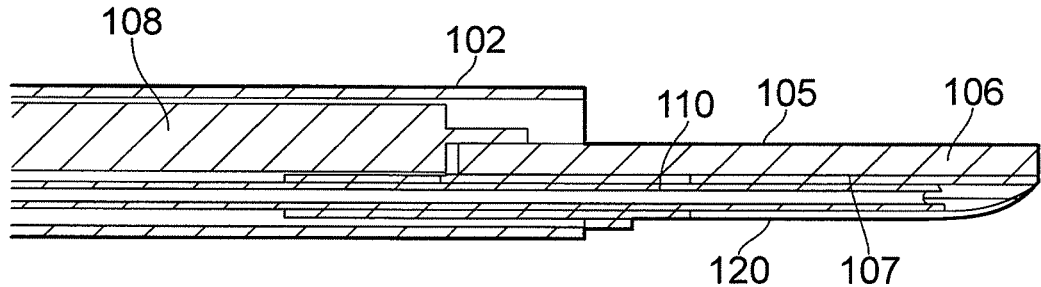
FIG. 5 is a cross-sectional side view through the instrument of FIG. 1.

As seen most clearly in FIG. 2, the distal end of the dielectric block is formed in a curved, e.g. parabolic, shape. This shape is preferred so that the instrument does not present sharp corners at its outer edges, and to enable use in multiple directions of travel. Such sharp corners can be undesirable when the instrument is used in environments with delicate tissue structures, such as the gastrointestinal tract, where the bowel wall is very thin.

The sleeve 102 defines a lumen which carries a flexible coaxial feed cable 108 and a fluid delivery structure. In this embodiment, the fluid delivery structure includes a passageway formed by space in the lumen around the flexible feed cable 108 and a retractable needle 110. The sleeve 102 carries a control wire 112 for both deploying and retracting the needle 110. Operation of the needle is described below.

The inner conductor 114 of the coaxial feed cable 108 protrudes from the distal end of the coaxial feed cable 108 and is electrically bonded (e.g. using solder) to the upper layer 105 of metallisation (first conductive element). The outer conductor of the coaxial cable 116 is electrically coupled to the lower layer of metallisation 107 (second conductive element) by a braid termination 118. The braid termination 118 comprises a tubular part that is electrically bonded to the outer conductor and a distally extending plate part 109 that fits under the dielectric block 106 and is electrically connected to the lower layer 107 of metallisation.

In this embodiment, a shaped piece of dielectric material 120 is attached to the lower surface of the dielectric block 106. It may be secured to the lower layer 107 of metallisation. The underside of the shaped piece of dielectric material 120 has a configuration particularly suited for use in procedures performed in the gastrointestinal tract. In the longitudinal direction, the shaped piece of dielectric material 120 comprises a distal part which gradually tapers (e.g. in a curved manner) towards the dielectric block 106. This part of the instrument is in closest proximity to the tissue being treated in use, e.g. the bowel wall, the wall of the oesophagus, the portal vein, or the pancreatic duct. By presenting a curved surface in this way, unwanted perforation of the bowel wall or the wall of the oesophagus or damage to the portal vein or the pancreatic duct can be avoided.

As can be seen most clearly in FIG. 2, the undersurface of the shaped piece of dielectric material 120 has a longitudinally extending recessed channel 122. The recessed channel defines an access path for the retractable needle 110. The recessed nature of the channel means that the access path is flanked one both sides by longitudinally extending ridges 124 of the shaped piece of dielectric material.

Figure 12A:
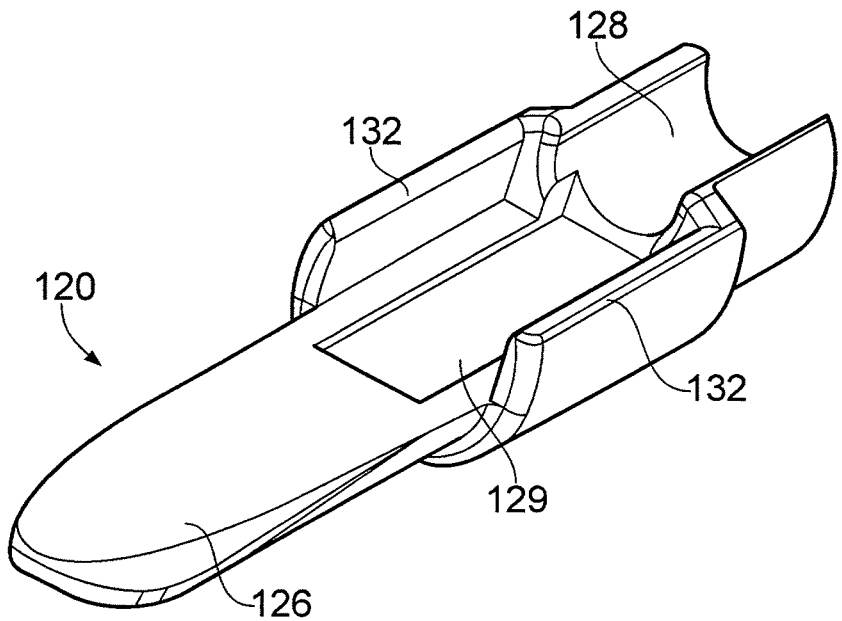
FIGS. 12A and 12B are perspective front and rear views respectively of a protective hull member suitable for use with the present invention.
Figure 12B:
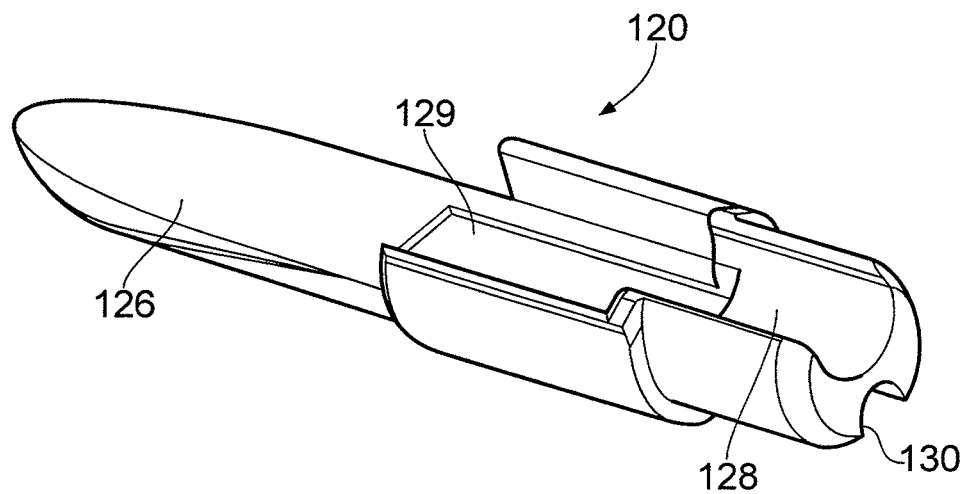

The surface of the shaped piece of dielectric material 120 that engages with the underside of the radiating spatula structure is shown in more detail in FIGS. 12A and 12B. The distal end of the shaped piece of dielectric material 120 has a flat upper surface 126 for contacting the lower layer of metallisation 107. A rectangular recess 129 is formed towards the proximal end of the flat upper surface 126 for receiving the plate part 109 of the braid termination 118.

The proximal end of the shaped piece of dielectric material 120 is formed with a U-shaped channel 128 for receiving and supporting the distal end of the coaxial feed cable 108. FIG. 12B shows that a similar channel 130 is formed on the underside of the proximal end of the shaped piece of dielectric material 120 to receive a guide conduit for the retractable needle (see FIGS. 6 and 7). The outer surface of the proximal end of the shaped piece of dielectric material 120 is cylindrical, with a diameter selected to fit inside the sleeve.

At the sides of the shaped piece of dielectric material 120 between the proximal and distal ends, there are a pair of upstanding wing portions 132, whose inner surfaces engage with respective side edges of the radiating spatula structure and whose outer surface engage in an interference fit with the inner surface of the sleeve 102.

The shaped piece of dielectric material 120 is preferably made from a ceramic or other material having low thermal conductivity.

In another embodiment, the dielectric body 106 and the shaped piece of dielectric 120 may be formed in one piece, i.e. as a unitary body. The unitary body may have a planar slot formed (e.g. cut) therein for receiving a conductive material to form the lower layer of metallisation (second conductive element). The thickness of the slot and therefore the lower layer of metallisation may be 0.1 mm or more, but preferably no more than 0.2 mm.

The overall size of the instrument may be such that it is suitable for insertion through the instrument channel of an endoscope. Thus, the outer diameter of the sleeve may be 2.8 mm or less, e.g. 2.7 mm.

Figure 6:
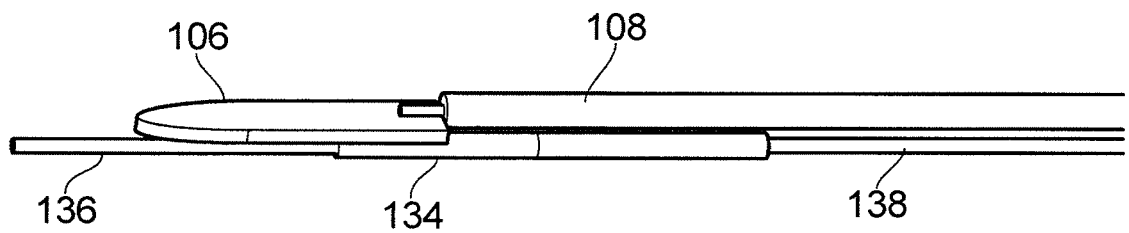
FIG. 6 is perspective view of the radiating section and retractable needle of an electrosurgical instrument according to the invention showing the needle in a deployed configuration.
Figure 7:
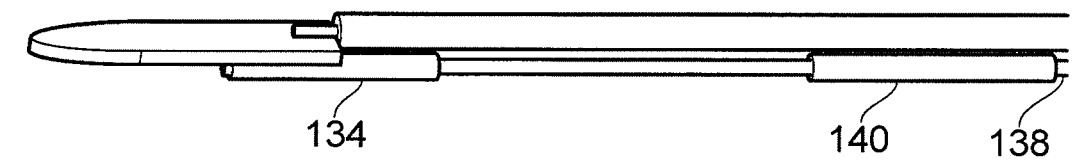
FIG. 7 is a perspective view of the radiating section and retractable needle of FIG. 6 showing the needle in a retracted configuration.
Figure 7A:
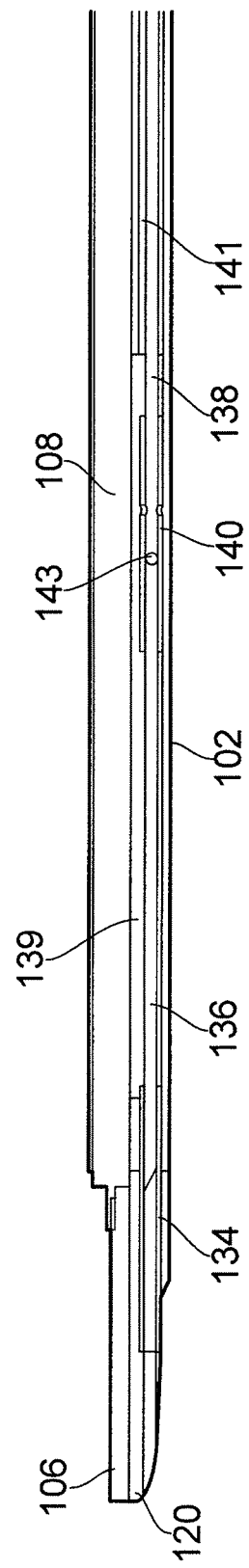
FIG. 7A is a cross-sectional view of the retractable needle mounted in the instrument.

FIGS. 6, 7, and 7A illustrate operation of a control wire 138 for deploying and retracting a retractable needle 136. The sleeve 102 and shaped piece of dielectric material 120 are omitted in FIGS. 6 and 7 for clarity. The retractable needle 136 is slidably mounted in a needle sleeve 134, which is fixed in the channel 130 formed in the underside of the shaped piece of dielectric material 120. The retractable needle 136 is capable for sliding between a deployed position (shown in FIG. 6), where it protrudes from the distal end of the instrument, and a retracted position (shown in FIG. 7) where the distal end of the needle is set back from the distal end of the instrument. The retractable needle 136 is attached at the end of a needle base unit 140, which is itself slidable within the sleeve by operating (i.e. pushing or pulling as appropriate) a suitable control wire 138, as is conventional. The control wire 138 is preferably welded in-line with the needle 136 as shown in FIGS. 6 and 7, as this allows a more compact arrangement. Alternatively, the control wire may abut against a side surface of the needle or needle base unit, as shown in FIG. 1.

When the control wire 138 pushes the needle 136 to its forward-most (i.e. deployed) position the needle base unit 140 abuts the needle sleeve to create a seal. The needle base unit 140 prevents the needle from being pushed too far out of the instrument. As shown in FIG. 7A, the space 139 in the lumen outside the coaxial cable 108 and retractable needle 136 forms a passageway for carrying fluid from the proximal end of the sleeve, where for example it may be injected by a user. An aperture 143 (seen in FIG. 7a) formed in a side wall of the needle base unit 140 provides a fluid flow path between the space 139 in the lumen and the proximal end of the needle 136. This enables fluid that has travelled down the length of the fluid conduit within the sleeve 102 to access the proximal end of the needle and be injected out through the needle tip.

As shown in FIG. 7A, the control wire slides in a guide conduit 141, which can prevent buckling of the control wire when it is under compression, thereby improving accuracy of control over the needles position. The guide conduit 141 may be formed in a semi-rigid insert mounted in the sleeve, as discussed below with reference to FIGS. 10 and 11.

In the retracted position, the distal end of the needle 136 (i.e. the needle tip) may be enclosed by the needle sleeve 134 to prevent accidental snagging on either patient tissue or the internal structure of an endoscope. The needle 136 may be a hypodermic needle terminating with a sharp point for penetrating biological tissue.

Injection of fluid (saline or the like) to plump up or raise the biological tissue may be particularly useful where the instrument is to treat the wall of the bowel or the wall of the oesophagus. For example, the instrument may be particular useful for removing sessile polyps, which sit flat on the wall of the bowel. Plumping up the tissue in this manner may help to reduce risk of bowel or oesophagus perforation. It is advantageous to be able to use the same instrument to deliver fluid as delivers RF and/or microwave energy since deflation (e.g. due to fluid seepage) may occur if a separate instrument is introduced into the region or during treatment. The ability to introduce fluid using the same treatment structure enables the level to be topped up as soon as deflation occurs. Moreover, the use of a single instrument to perform desiccation or dissection as well as to introduce fluid also reduces the time taken to perform the polyp removal procedure, reduces the risk of causing harm to the patient and also reduces the risk of infection. More generally, injection of fluid may be used to flush the treatment region, e.g. to remove waste products or removed tissue to provide better visibility when treating. This may be particularly useful in endoscopic procedures.

Figure 8:
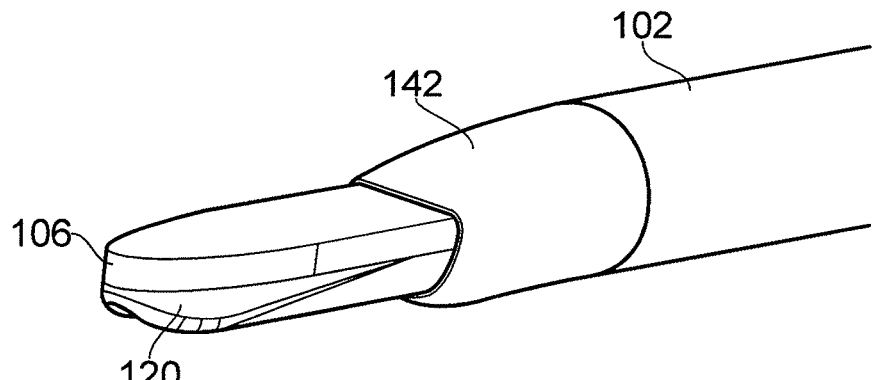
FIG. 8 is a perspective view of the end of an electrosurgical instrument according to an embodiment of the invention.

FIG. 8 shows a view of the instrument tip, in which the distal end of the sleeve 102 is "potted" in a cap element 142, which covers the electrical joint between the radiating spatula structure and the coaxial cable. The cap element 142 may be formed from a suitable a heat shrink material or from potting adhesive, e.g. UV curable adhesive such as Loctite® 4304 and/or Loctite® 4305. Protecting the joint in this way may prevent arcing from occurring at the electrical joint during use. The adhesive used should not be lossy or absorb energy at the microwave frequency of choice. Using a small amount of adhesive will also minimise the amount of energy coupled into it. If microwave power is absorbed by the adhesive, it will cause local heating and loss of microwave power available at the edges of the blade.

Figure 9:
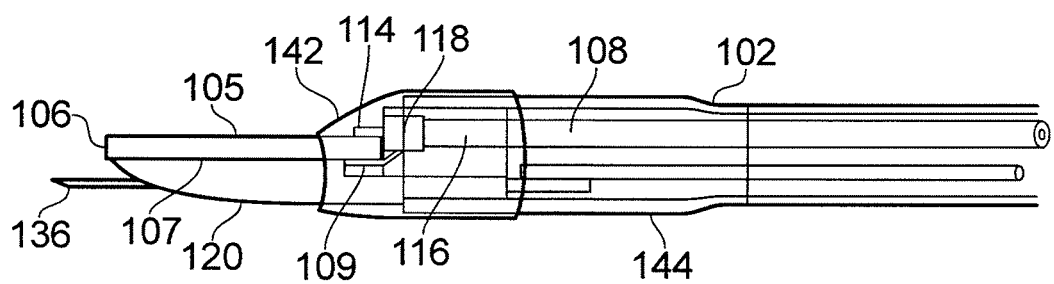
FIG. 9 is a cross-section side view through the instrument shown in FIG. 8.

FIG. 9 shows a schematic cross-section view of the distal end of the instrument. In this view the needle 136 is deployed. Here the distal end of the sleeve 102 includes a widened portion 144 having an increased diameter. The widened portion 144 provides more space at the distal end, which gives more room for the needle deployment mechanism and a more robust connection between the coaxial cable 108, radiating spatula structure 105, 106, 107 and shaped piece of dielectric material 120.

Figures 10, 11:
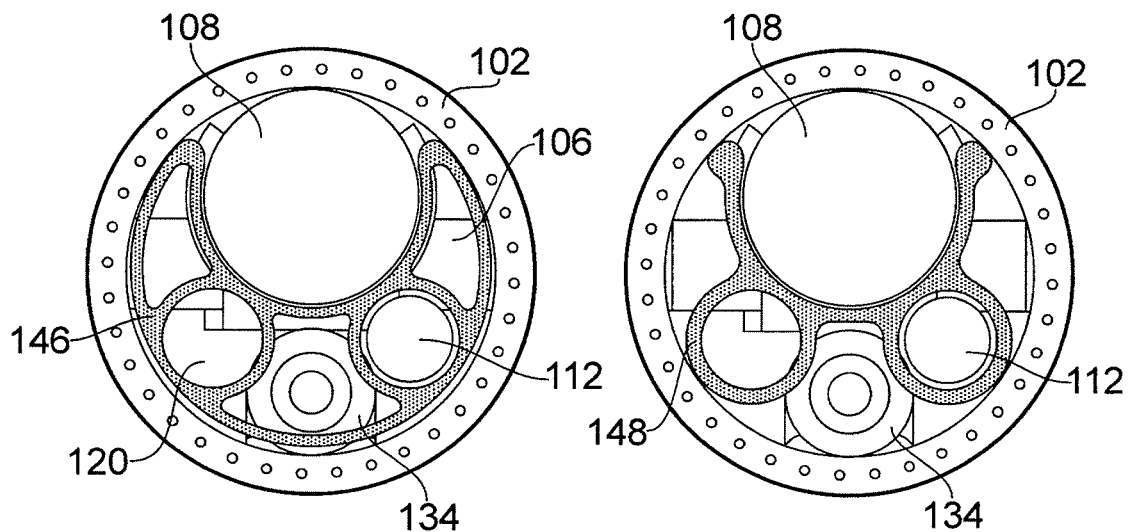
FIG. 10 is a cross-section view through the shaft of an electrosurgical instrument according to one embodiment of the invention.
FIG. 11 is a cross-section view through the shaft of an electrosurgical instrument according to another embodiment of the invention.

FIG. 10 shows a cross-section view through the sleeve 102 facing towards the distal end of the instrument. Mounted within the sleeve 102 is a semi-rigid insert 146 that is arranged to maintain the position of the coaxial cable 108 and push wire 112 along the length of the sleeve 102. The insert 146 may be a length of extruded plastic material or the like. In FIG. 10 the insert 146 has a horse-shoe shaped cross-section, with an outer surface for engaging the inner surface of the sleeve, and a U-shaped channel for receiving the coaxial cable 108. Two longitudinally extending circular passages are formed within the insert for carrying the push wire and for providing space for a fluid path respectively. Maintaining the position of the push wire is important, because if movement of the push wire is unconstrained within the lumen of the sleeve, control of the wire can be lost e.g. due to the push wire moving laterally within the sleeve.

Although shown as a separate insert in this embodiment, these passages may be incorporated into the sleeve itself, e.g. as a single extrusion or through bonding or welding to the inner surface of the sleeve 102. The insert may exhibit lateral strength to provide crush resistance and durability to the device.

FIG. 11 shows a similar view to FIG. 10 for another extruded rigid insert 148. The effect of the semi-rigid inserts 146, 148 is to provide multiple lumens within a common sleeve 102.

When used to deliver microwave frequency energy, the radiating spatula behaves as a resonant microwave structure, fed from a coaxial transmission line. Its function is to pass microwave energy into biological tissue that is close to or touching the region near the tip of the spatula. As mentioned above, the distal end of the radiating spatula blade is curved to avoid presenting sharp edges or corners to tissue in use. A discussion of the effect of changing the shape of the end of the spatula on the delivery of microwave energy is presented below with reference to FIGS. 13 to 23.

The spatula is a low impedance planar transmission line, that is to say that the ratio of the voltage between the top and bottom metal plates to the (equal and opposite) currents in the two plates is close to 30Ω (calculated using microwave field modelling software). Typically, the transmission line feeding the spatula has an impedance of 50Ω. Thus, the transmission line and the biological tissue touching the end of the spatula appear as high impedances to the spatula.

The difference in impedance at each end would normally present a partial obstacle to the passage of power into and out of the spatula. However, when the spatula is close to a whole number of half-wavelengths long, the voltages at the end of the spatula increase, and the currents at the end decrease, both due to a resonant effect, so that power passes readily from the coaxial line through the spatula into the tissue. For this reason the length of the spatula, from the end of the coaxial transmission line to the other end of the spatula (or planar transmission line), plays a significant role in the effectiveness of the spatula.

The length of the spatula is carefully adjusted so that, taking into account the modification of the wavelength by the shape of the spatula, the dielectric constant of the material between the plates, and fringing fields at each end of the spatula, the spatula is close to one half wavelength long at the operating frequency. In practice this length can be found empirically by numerical simulation and/or experiment.

The effect of changes in shape in the end of the spatula can be understood in terms of a change in the capacitance of the end of the spatula.

Figure 13:
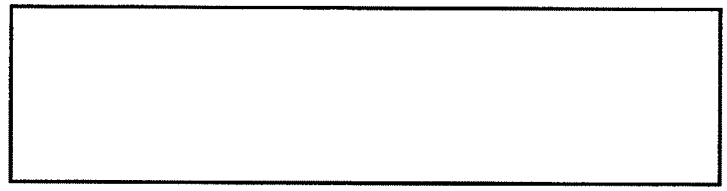
FIGS. 13 to 16 illustrate how the length of the spatula may be adapted as its end is curved.
Figure 14:
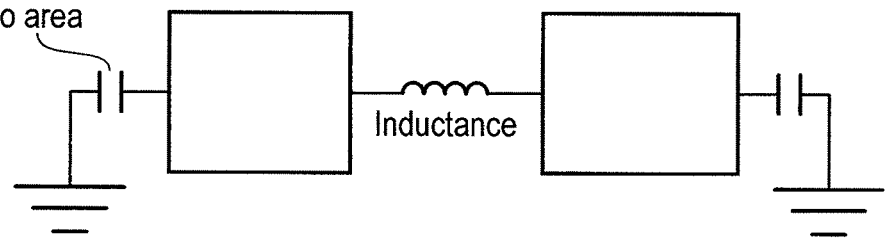

Under resonant conditions, the centre of the rectangular spatula shown in FIG. 13 behaves in a similar way to an electrical inductance (coil) and each end behaves similarly to a capacitor, as shown schematically in FIG. 14. The product of the capacitance and the inductance is proportional to the inverse square of the frequency at which the spatula will resonate. This is described by the standard electrical relation $$f = \frac{1}{2\pi\sqrt{LC}}$$

for the resonant frequency f of a resonant electrical circuit with a capacitance C and an inductance L.

If the shape of the end of the spatula is changed, this results in a change in capacitance so that the resonant frequency of the spatula changes, or to put it another way the spatula is now not the correct length to resonate at the operating frequency.

The overall length of the spatula can, however, be adjusted to bring it back into resonance. A good approximation to the length adjustment needed is that required to return the area of the spatula to the value before the end was rounded—this is equivalent to adjusting the capacitance back to its previous value.

Capacitance is proportional to the area of the capacitor. If the end of the spatula were rounded off to a semi-circle or ellipse, then the length should be increased so that the extra rectangular part has the same area as the parts cut off to make the semi-circular end, as indicated in FIG. 15.

Figure 15:
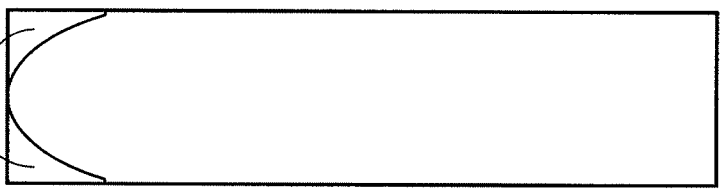

The missing area in FIG. 15 is $$2r_1 r_2 - \frac{\pi r_1 r_2}{2} \approx 2r_1 \times 0.21462 r_2$$

where $r_1$ is half the width of the spatula and is the half-length of the ellipse that forms the curved end.

Figure 16:
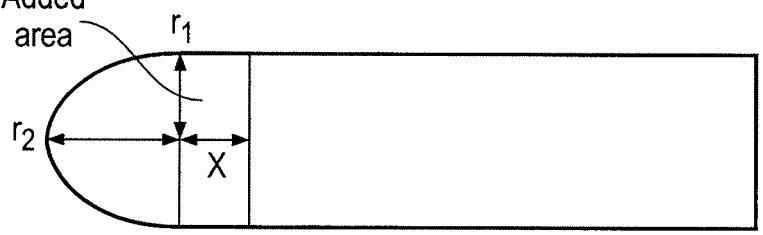

The area of the rectangle to be added shown in FIG. 16 is $$2r_1 x = 2r_1 \times 0.21462 r_2$$

where x is the extra length required.

Thus the extra length required is approximately 0.215 times the length of the rounded part of the spatula. If the rounded end is 3 mm long, the extra length required is about 0.64 mm. This increase in length was tested by simulation with the actual shape of the spatula and found to be close to the optimum. The length of the model was adjusted empirically to find the optimum, which was actually 0.6 mm.

The change in resonant frequency may also be corrected by changing the capacitance of the other end of the spatula, by changing the geometry of the connection to the 50Ω coaxial cable. A simple way to do this is to change the spacing between the top plate of the spatula and the coaxial line.

Figure 17:
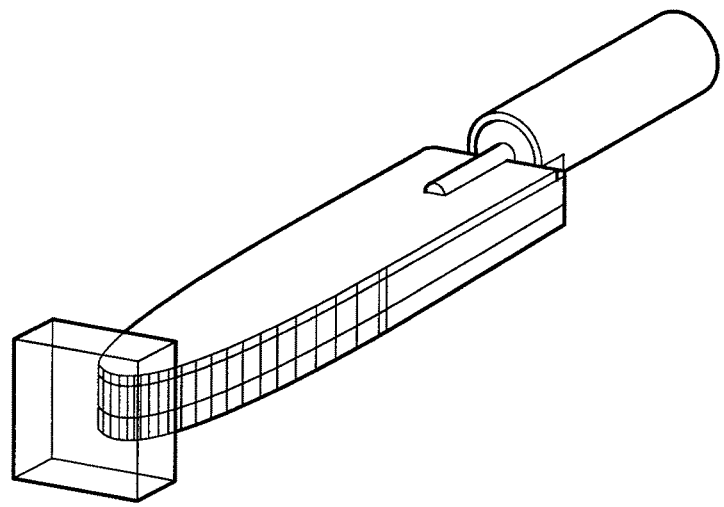
FIGS. 17 to 20 show views of a simulation configuration for a spatula with differing gaps between the top conductor of the spatula and the coaxial feed.
Figure 18:
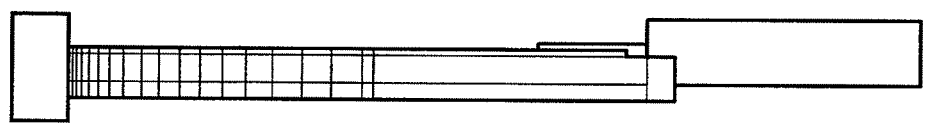
Figure 19:
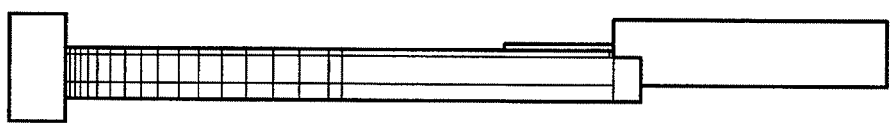

The general shape of the spatula is shown in FIG. 17, and a side view of the spatula with 0.4 mm gap is shown in FIG. 18. A side view of the spatula with 0.1 mm gap is shown in FIG. 19, and a close up side view in FIG. 20.

Figure 20:
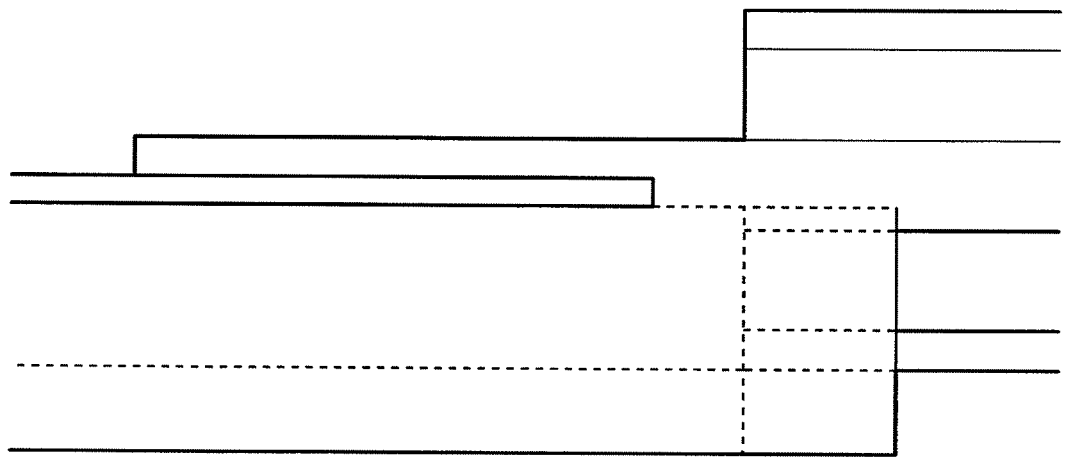

In FIG. 20, the gap between the top plate of the spatula and the coaxial line forms a capacitor that can be used to adjust the resonant frequency of the spatula. If the gap is reduced, the capacitance increases, and the resonant frequency drops.

Figure 21:
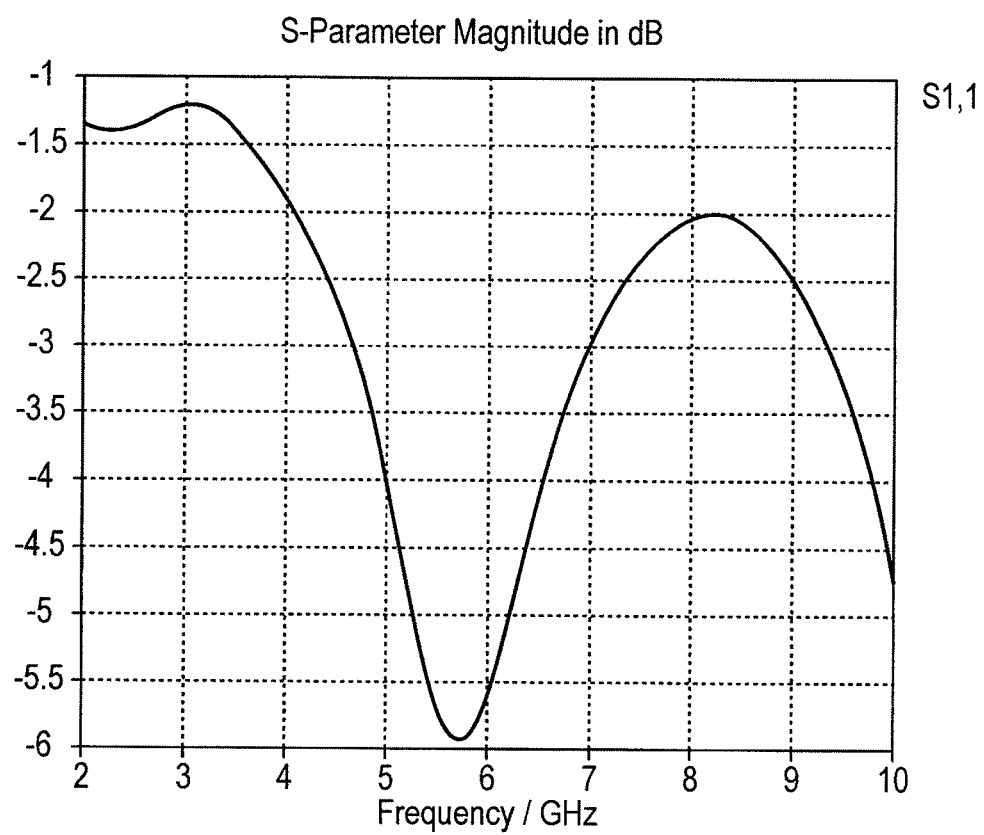
FIGS. 21 to 23 are graphs showing the return loss for spatulas having different gaps between the top conductor of the spatula and the coaxial feed.

FIG. 21 shows the return loss for the 10.6 mm long spatula with a 0.4 mm gap. The best return loss is close to 5.8 GHz.

Figure 22:
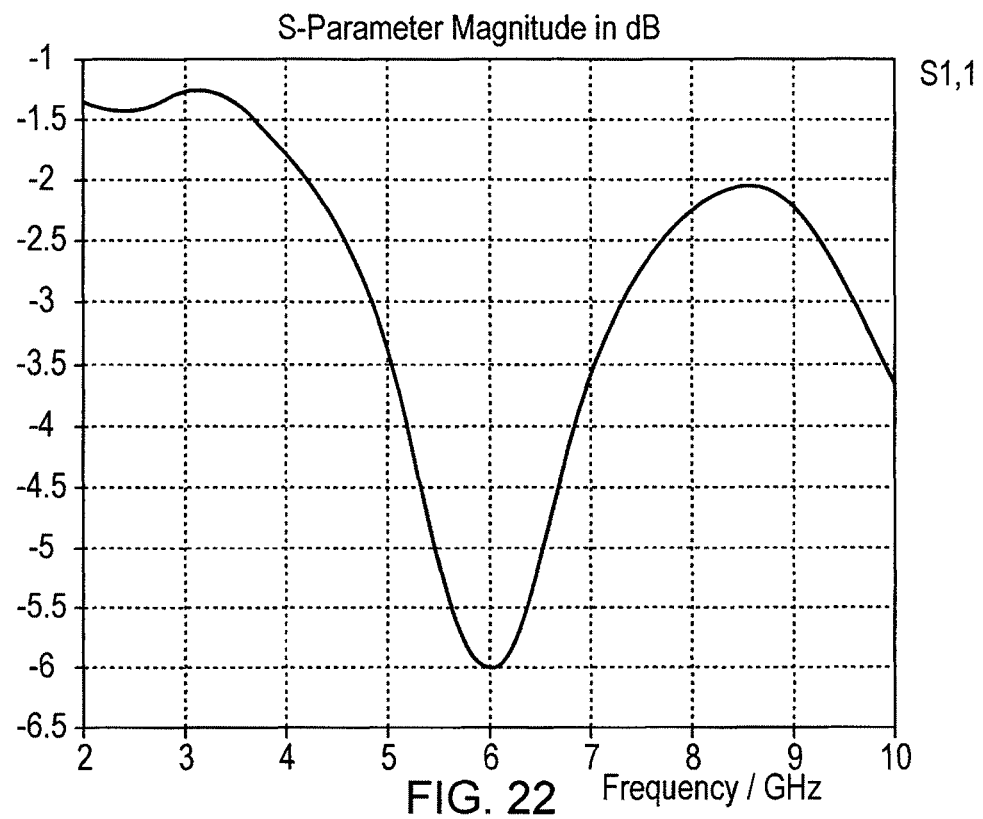
Figure 23:
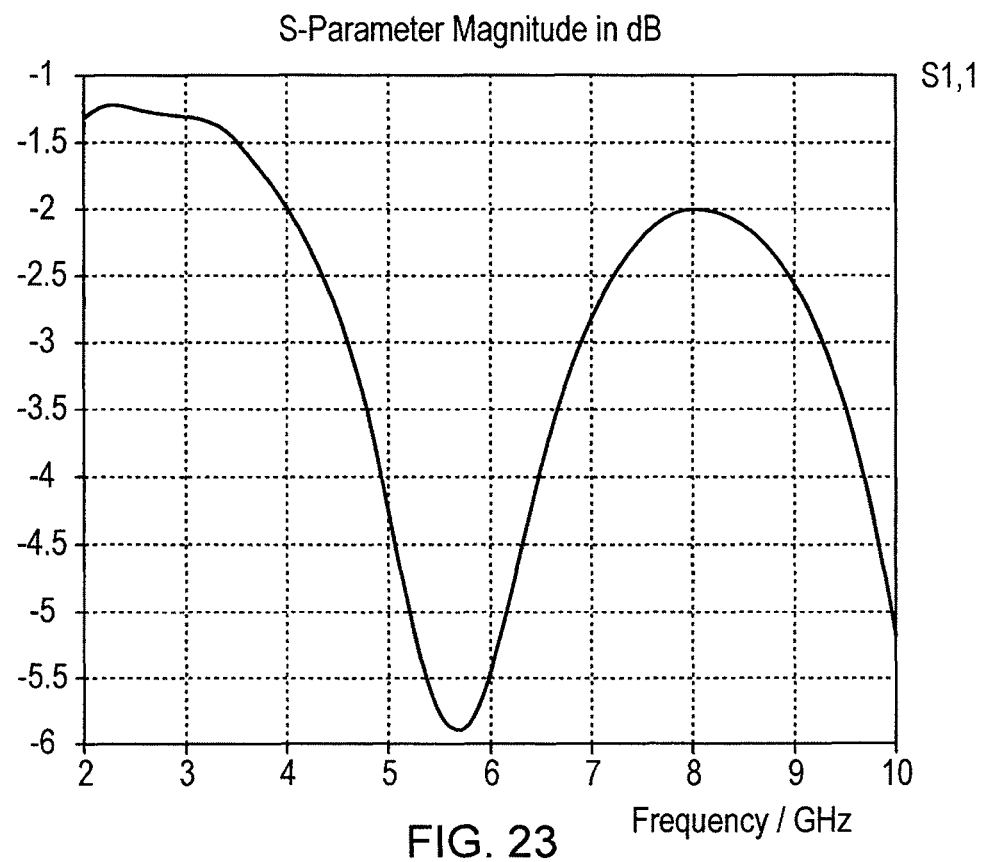

FIGS. 22 and 23 compare the return loss for a 10 mm long spatula with 0.3 mm and 0.1 mm gaps respectively. It can be seen in FIG. 22 that with the 0.3 mm gap the best return loss is at 6 GHz, and in FIG. 23 with a 0.1 mm gap the best return loss is close to 5.8 GHz.

It may be difficult to accurately manufacture the device with a 0.1 mm gap, so the solution of increasing the spatula length to adjust for changing the overall shape may be preferred. However, other ways of increasing the capacitance at the cable end of the spatula might be used, such as increasing the thickness of the top plate, which may happen anyway when solder is applied.

Because it may be difficult to accurately describe the geometry that is actually achieved around the connection between the cable and the spatula, the best approach is to aim for a geometry that is easily built and is repeatable.

The invention claimed is:

1. An electrosurgical resection instrument for applying to biological tissue radiofrequency (RF) electromagnetic (EM) energy, the instrument comprising:
   an instrument tip comprising a planar body made of a first dielectric material separating a first conductive element on a first surface thereof from a second conductive element on a second surface thereof, the second surface facing in an opposite direction to the first surface;
   a coaxial feed cable comprising an inner conductor, an outer conductor coaxial with the inner conductor and a second dielectric material separating the inner and outer conductors, the coaxial feed cable being for conveying an RF signal; and
   a protective hull comprising a third piece of dielectric material mounted to form an underside of the instrument tip,
   wherein the inner conductor is electrically connected to the first conductive element and the outer conductor is electrically connected to the second conductive element to enable the instrument tip to receive the RF signal, and
   wherein the first and second conductive elements extend up to a distal side edge of the planar body to form an RF cutting portion in which the first and second conductive elements act as active and return electrodes to emit RF EM radiation corresponding to the RF signal from the distal side edge of the planar body, and
   wherein the protective hull has a smoothly contoured convex undersurface facing away from the planar body, the undersurface comprising a longitudinally extending recessed channel formed therein between a pair of ridges.

2. The instrument according to claim 1, wherein the smoothly contoured convex undersurface of the protective hull smoothly tapers at a perimeter to meet the distal side edge of the planar body.

3. The instrument according to claim 1, wherein a thickness of the protective hull decreases towards a distal end of the instrument tip.

4. The instrument according to claim 1, wherein a separation of the first and second conductive elements at the distal side edge is less than 1 mm.

5. The instrument according to claim 1, wherein the first and second conductive elements each comprise layers of metallisation, the layers of metallisation being formed on opposite surfaces of the first dielectric material.

6. The instrument according to claim 5, wherein each layer of metallisation comprises a plated region formed from a metal having a melting point higher than 1500° C.

7. The instrument according to claim 6, wherein the first conductive element comprises a first connecting portion between the plated region and the inner conductor and the second conductive element comprises a second connecting portion between the plated region and the outer conductor, wherein the first and second connecting portions are made from a conductive material having melting point less than 1200° c.

8. The instrument according to claim 7, wherein the conductive material is at least one of silver or gold.

9. The instrument according to claim 6, wherein the metal is at least one of titanium or tungsten.

10. The instrument according to claim 1, wherein the protective hull is formed from ceramic or biocompatible plastic.

11. The instrument according to claim 1, wherein the protective hull and first dielectric material are formed in one piece as a unitary body.

12. The instrument according to claim 1, wherein the instrument tip has a curved distal edge.

13. The instrument according to claim 1, including a fluid feed conduit for conveying fluid to the instrument tip for delivery out of the instrument.

14. The instrument according to claim 13, wherein the fluid feed conduit comprises a sleeve that defines a lumen for transporting fluid to the instrument tip, the sleeve having the instrument tip body and protective hull secured at a distal end thereof, and being arranged to carry the coaxial cable in the lumen.

15. The instrument according to claim 14, including a fluid delivery mechanism mounted at the distal end of lumen of the sleeve, the fluid delivery mechanism being operable to deliver fluid from the lumen through the protective hull.

16. The instrument according to claim 15, wherein the fluid delivery mechanism includes a retractable needle mounted beneath the planar body in the recessed channel of the protective hull.

17. The instrument according to claim 16, wherein the retractable needle is movable in a longitudinal direction between a deployed position in which the retractable needle protrudes beyond a distal end of the instrument tip and a retracted position in which the retractable needle is set back from the distal end of the instrument tip.

18. The instrument according to claim 14, wherein the sleeve has longitudinal braids therein to assist in a transfer of torque from a proximal end to the instrument tip.

19. The instrument according to claim 14, wherein the sleeve comprises a multi lumen tube.

20. The instrument according to claim 19, wherein the sleeve includes an extruded separator element inserted inside a single lumen tube, the extruded separator element including a U-shaped channel for guiding the coaxial cable and one or more longitudinal passages for fluid to flow along the sleeve.

21. The instrument according to claim 14, wherein the sleeve has an outer diameter of 2.8 mm or less.

22. The instrument according to claim 14, including a cap element at the distal end of the sleeve, a cap element covering an electrical joint between the coaxial cable and the first and second conductive elements.

23. The instrument according to claim 14, wherein the cap element is formed from an impermeable insulating potting material.

24. The instrument according to claim 1, wherein the coaxial cable is arranged to convey a microwave signal separately from or simultaneously with the RF signal, and wherein the first and second conductive elements are arranged on the first dielectric element to act as an antenna to radiate microwave EM radiation corresponding to the received microwave signal.

* * * * *